United States Patent [19]

Björk et al.

[11] 4,308,387
[45] Dec. 29, 1981

[54] DIPHENYLBUTYL-PIPERZINECARBOXA-MIDES

[75] Inventors: Anders K. K. Björk, Bjärred; Knut G. Olsson, Malmö; Aina L. Abramo, Bjärred; Erik G. Christensson, Lund, all of Sweden

[73] Assignee: AB Ferrosan, Malmö, Sweden

[21] Appl. No.: 86,068

[22] Filed: Oct. 18, 1979

[30] Foreign Application Priority Data

Oct. 20, 1978 [SE] Sweden ............................... 7810971

[51] Int. Cl.³ ................. C07D 295/10; A61K 31/495
[52] U.S. Cl. ..................................... 544/390; 424/250
[58] Field of Search ......................................... 544/390

[56] References Cited

FOREIGN PATENT DOCUMENTS 123240  5/1972  Denmark ........................... 544/402
51-8283  1/1976  Japan ................................. 544/390

OTHER PUBLICATIONS

Irikura, "Chem. Abs.", vol. 85, (1976), 33082m.

Primary Examiner—Anton H. Sutto
Attorney, Agent, or Firm—Haseltine and Lake

[57] ABSTRACT

Compounds having the general formula

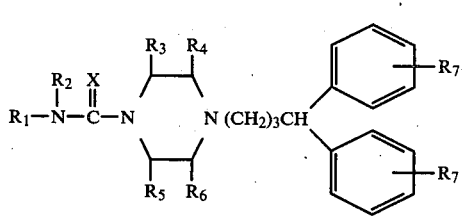

as herein defined and pharmaceutically acceptable acid addition salts thereof. Pharmaceutical compositions containing said compounds. Methods of treatment of humans and animals by such compounds and compositions.

3 Claims, 4 Drawing Figures

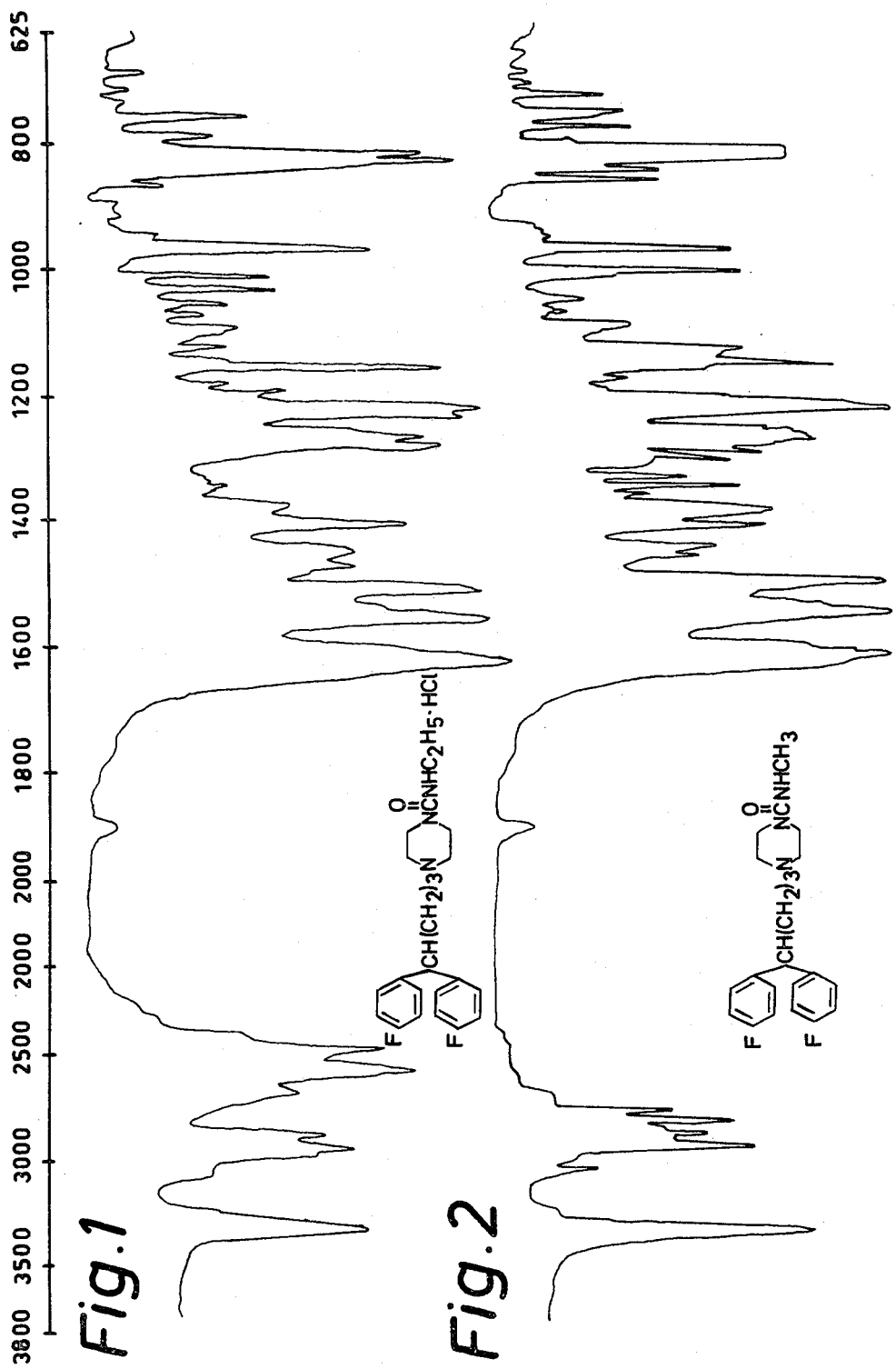

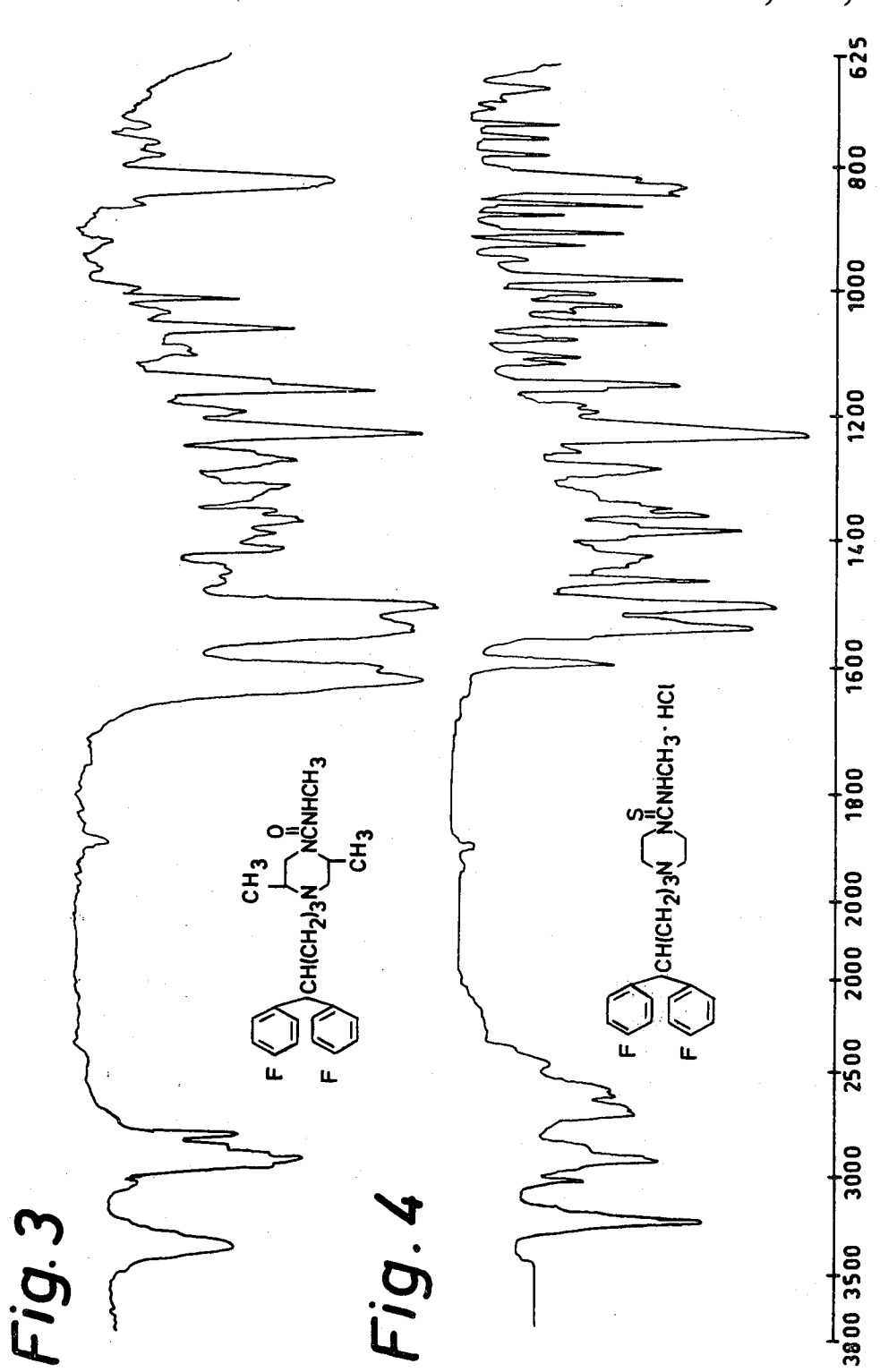

DIPHENYLBUTYL-PIPERZINECARBOXAMIDES

This invention relates to a novel class of N',N',2,3,4,5,6-substituted 1-piperazine-carboxamides and carbothioamides, acid addition salts thereof, pharmaceutical compositions containing the same, and methods of making and using the same.

Most drugs used today in the treatment of different mental disorders are contained in the groups of antidepressants, anxiolytics and the major tranquillisers, i.e. neuroleptics. All said drugs have been shown to be useful in the treatment of mental disorders, but they also have considerable disadvantages. Thus, the efficacy of the antidepressants is only about 60% and their anticholinergic effect as well as their cardiovascular side effects cause major disadvantages. Among the anxiolytics non-toxic compounds are found, but they are all liable to induce dependence and abuse. The neuroleptic drugs are useful in the suppression of symptoms of schizophrenia but their greatest disadvantage is that they induce severe extrapyramidal side effects some of which are not reversible, i.e. tardive dyskinesia. They also induce mental side-effects, e.g. reduced emotional feelings especially in non-psychotic patients. It must be remembered that all neuroleptics act by an unspecific interference with the dopaminergic transmission in the brain, although it has never been proved that their antipsychotic action results from the antidopaminergic, i.e. dopaminereceptor blocking, activity. Dopaminergic transmission in the brain is involved in motoric functions but also in behavioural, endocrine and autonomic functions. Therefore, the rather unspecific antidopaminergic activity may product many kinds of side-effects. Thus, there is ample evidence that the extrapyramidal side effects mentioned above result from this blocking.

Most neuroliptics also induce a severe sedation. In many cases it is therefore difficult to decide whether e.g. the antiagressive properties of neuroleptic drugs is due to a lack of coordination of muscular activity (ataxia, immobility or catalepsy) or to a real anti-aggressive property inherent in the drug.

The novel 1-piperazine-carboxamides and carbothioamides according to the invention may be structurally represented by the general formula I

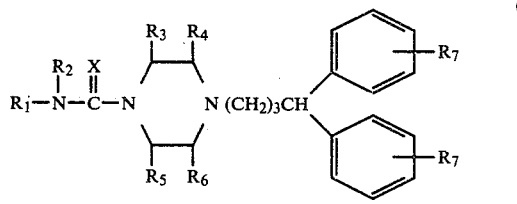

wherein $R_1$ and $R_2$ are groups independently selected from the group of hydrogen, alkyl straight or branched chains having from 1 to 10 carbon atoms, cycloalkyl having from 3 to 8 carbon atoms, aralkyl having from 7 to 9 carbon atoms, alkenyl having from 2 to 10 carbon atoms, phenyl unsubstituted or substituted by one to three substituents selected from halogen, including F, Cl and Br, lower alkyl having from 1 to 5 carbon atoms, lower alkoxy having from 1 to 5 carbon atoms, amine unsubstituted or substituted by one or two lower alkyl groups having from 1 to 5 carbon atoms, —$CF_3$ and —CN groups, $R_3$, $R_4$, $R_5$ and $R_6$ are groups independently selected from hydrogen, lower alkyl having from 1 to 3 carbon atoms and phenyl, $R_7$ is a group selected from hydrogen, halogen including F, Cl and Br, lower alkyl having from 1 to 3 carbon atoms and —$CF_3$ groups, and X is O or S, and pharmaceutically acceptable acid addition salts thereof.

The compounds of formula I have a new pharmacological profile not seen in any compound described earlier. If given to male mice made aggressive by solution they induce a potent and longlasting inhibition of this aggression without causing any ataxia or catalepsy. Furthermore, in mice the compounds of formula I have a good reducing effect on excitation and insomnia during anaesthesia.

In contrast to neuroleptics the new compounds of formula I do not inhibit apomorphine or amphetamine induced stereotypies or hypermotility which means that they are not potent dopaminereceptorantagonists. In higher doses the new compounds decrease exploratory behaviour and have influence on condition avoidance response. These and other findings suggest that the compounds have antipsychotic properties. In low doses the compounds induce behavioural effects in monkeys which are similar to what is seen after antidepressants. This means that the compounds will be useful in the treatment of depressions. Furthermore, the new compounds show valuable analgesic properties, which are not reversed by naloxone. Contrary to morphine the compounds have not been found to create physical dependence on chronic administration.

The antianxiety and the protecting effect against induced stress shown by the compounds of formula I will be of value in the treatment of psychosomatic disorders and of ulcus in man. Furthermore, the anti-inflammatory effect of the compounds, the effects on the immunologic system as well as the psychotrophic effects underline their use in geriatric and depressed patients.

A unique binding proflie of the compounds to specific binding sites in the membranes of different tissues can be utilized in modulating ion-dependent processes, secretion, metabolism and aggregation of cells as well as vascularization of different tissues. Some of these effects are manifested in a hypothermic response.

Based on these findings it is concluded that the compounds of formula I will be useful in the treatment of mental disorders in man as well as in animals although their pharmacological activities are different from those of the antidepressants, anxiolytics and neuroleptics now used in the clinic. The profile of action of the compounds of formula I suggests an influence on limbic, hypothalamic and pituital areas of the brain.

The new compounds seem to be useful in the treatment of aggressive behaviour in animals, especially in pigs, in promoting without bursts of aggression the development of a natural hierarchy in groups of animals and in calming of anxious and stressed animals.

According to the present invention the novel compounds of general formula I are prepared according to the following reaction sequences:

Sequence A (a) by reacting a 1-piperazinecarboxamide of formula II

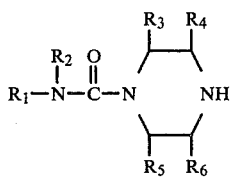
(II)

with a 4-substituted 1,1-diarylbutane of formula III

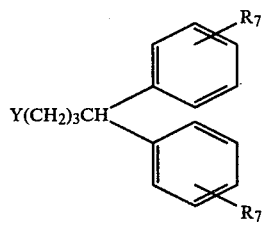
(III)

wherein $R_1$, $R_2$, $R_3$, $R_4$, $R_5$, $R_6$ and $R_7$ are as designed above and Y is selected from the group consisting of halogen, e.g. Cl, Br and I, and another reactive group, e.g. a mesyl or tosyl ester group, to produce a compound of formula I.

Sequence A (b) by reacting a 1-(4,4-diaryl-butyl)piperazine of formula IV

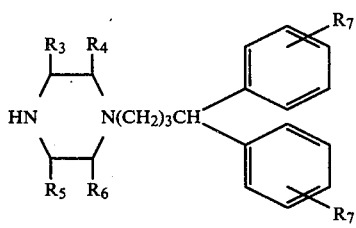
(IV)

with an isocyanate or isothiocyanate $R_1$—NCX, wherein X is O or S, or with a carbamoyl chloride or thiocarbamoyl chloride

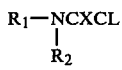

to produce a compound of formula I.

Sequence A (c) by reacting a 1-(4,4-diaryl-butyl)piperazine of formula IV with an alkali metal cyanate, preferably potassium cyanate, Metal-OCN to produce a compound of formula I wherein $R_1$ and $R_2$ are hydrogen.

Sequence A (d) by reacting a 1-(4,4-diaryl-butyl)piperazine of formula IV with a phenyl carbamate of formula VIII

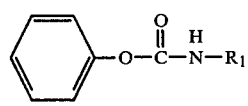
(VIII)

to produce a compound of formula I.

The 1-piperazinecarboxamides of formula II which are used in the method of the invention can be prepared by a sequence of reactions according to any of the following:

Sequence B (a) A reaction between an isocyanate $R_1$—NCO and a 1-benzylpiperazine of formula V

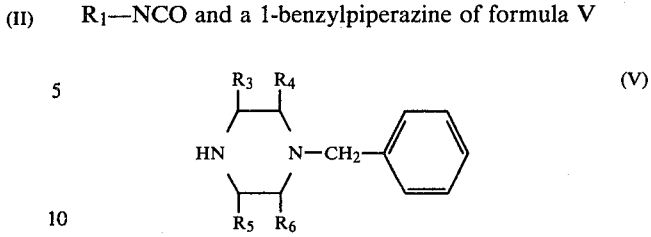
(V)

in ether or the like gives a compound of formula VI

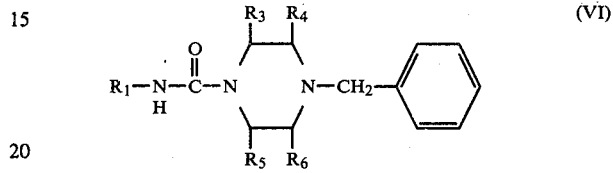
(VI)

Alkylation of the anion generated from the carboxamide of formula VI by treatment first with a suitable strong base, e.g. lithium diisopropylamide, in tetrahydrofuran and then with an alkyl halide $R_2$—Z wherein Z is selected from the group consisting of Br and I leads to the N′,N′-dialkylated compounds of formula VII

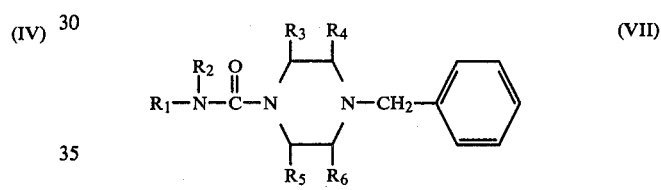
(VII)

The compounds of formulas VI and VII are hydrogenated over a noble metal catalyst to give the compound of formula II.

Sequence B (b) A reaction between a carbamoyl chloride

and a 1-benzylpiperazine of formula V in chloroform or the like gives a compound of formula VII. Debenzylation over a nobel metal catalyst gives the compound of formula II.

In sequence A (a) the compound of formula II is reacted with a compound of formula III (synthesised according to French Pat. No. M 3695) in a suitable solvent, e.g. a lower alkanol, such as methanol, ethanol, n-butanol and the like, in the presence of an acid acceptor, i.e. an appropriate base, e.g. an alkali metal carbonate or bicarbonate, which may be utilised to bind the acid that is liberated during the course of the reaction to give the compound of formula I. Elevated temperatures may be employed to enhance the rate of reaction.

In sequence A (b) the compound of formula IV (synthesised according to Neth. Appln. No. 6,507,312) is reacted with an isocyanate (or an isothiocyanate) $R_1$—NCX or a carbamoyl chloride (or a thiocarbamoyl chloride)

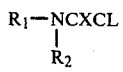

in a suitable solvent, e.g. diethyl ether, chloroform, toluene and the like to give the compounds of formula I. The mixture is reacted over a wide range of temperatures from about 10° C. to about 110° C., although it is possible to employ temperatures above and below this range.

In sequence A (c) the compound of formula IV is reacted with an alkali metal cyanate in an aqueous medium containing acetic acid to form the compound of formula I.

In sequence A (d) the compound of formula IV is reacted with a phenyl carbamate of formula VIII in a suitable solvent e.g. an aromatic hydrocarbon, i.e. benzene, toluene, xylene and the like in the presence of an appropiate base e.g. an alkali metal carbonate to form the compound of formula I. Elevated temperatures are employed to enhance the rate of reaction.

tration. The new compounds were found to be very potent in blocking this type of aggression.

The effect of drugs on the motor coordination is investigated by the performance of mice on the rotarod. The rotating rod test is a well-known test of ataxia in mice. The compounds listed in Table I were administered subcutaneously. The $ED_{50}$-value is the dose making 50% of the mice ataxic 1 hour after the drug administration. The new compounds of formula I do not produce ataxia at doses of $\leq 20$ mg/kg.

The compounds according to the invention have been found to have potent analgesic properties. The analgesic effect of the compounds is evaluated from the writhing syndrome which can be abolished by analgesics. The $Ed_{50}$-value is the subcutaneous dose making 50% of the mice free from symptoms of the writhing syndrome.

The $ED_{50}$-values expressed in milligrams per kilogram body weight in the anti-amphetamine test, in the inhibition of aggression test, in the spontaneous mouse killing test, in the rotarod test and in the writhing test are presented in Table I.

TABLE I

| Compound | $R_1$ | $R_2$ | $R_3$ | $R_6$ | X | Anti-amphetamine test | Isolation-induced aggressive behaviour test | Spontaneous mouse killing test | Rotarod test | Writhing test |
|---|---|---|---|---|---|---|---|---|---|---|
| I | $CH_3$ | H | H | H | O | >50 | 4.8 | 0.5 | >20 | 0.5 |
| II | $C_2H_5$ | H | H | H | O | >50 | 1.3 | 0.4 | >20 | 0.7 |
| III | $CH_3$ | H | $CH_3$ | $CH_3$ | O | >50 | 2.6 | 1.4 | >20 | 1.0 |
| IV | $CH_3$ | H | H | H | S | >50 | 2.0 | 0.07 | >20 | 1.4 |
| Azaperone | | | | | | — | 0.3 | >10 | 1.0 | — |
| Lenperone | | | | | | 0,1 | 0.3 | 1.0 | 1.0 | — |
| Diazepam | | | | | | — | 3.0 | 1.0 | 7.0 | — |
| Morphine | | | | | | — | — | — | — | 1.6 |

Conventional types of neuroleptics are potent inhibitors of amphetamine induced behavioural stereotypies. One determines in Sprague Dawley female rats the ability of subcutaneously administered compounds to inhibit compulsory gnawing and chewing responses to a subcutaneous dose of 10 mg/kg of amphetamine administered half an hour after the compound to be tested. The new compounds of formula I are weak antagonists in this test.

Male mice submitted to prolonged isolation develop aggressive behaviour against each other when paired. The isolation-induced aggressive behaviour test was used to determine tranquillising activity of the compounds listed in Table I (S. Garattini and E. B. Sigg, Aggressive Behaviour, 1969). Tests were conducted 60 minutes after subcutaneous drug administration. The new compounds of formula I are potent in this test.

Another model used in aggression, i.e. mouse killing (muricide) by rats, is based on existing interspecies aggression [(Karli, P., Behaviour 10, 81 (1956)]. In Long Evans male rats mousekilling is still a spontaneous behaviour. In the experiments Long Evans male rats were placed in individual cages and pretested to kill mice consistently within 5 minutes after confrontation. Tests were conducted 60 minutes after subcutaneous adminis- The formula I bases are convertible to therapeutically active non-toxic acid addition salts by treatment with an appropriate acid, e.g. an inorganic acid, such as a hydrohalic acid, especially hydrochloric and hydrobromid acid, or sulfuric acid, nitric acid, phosphoric acid and the like, or an organic acid, such as acetic, propionic, glycolic, lactic, malonic, succinic, fumaric, tartaric, citric and the like acids. Conversely, the salt form can be converted by treatment with alkali into the free base form.

Effective quantities of any of the foregoing pharmacologically active compounds of formula I may be administered to a human being or animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier or excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards preferably 25, 50 or 100 milligrams or even higher depending on the condition to be treated and the age and weight of the patient as well as the response to the medication.

The unit dose may be from 0.1 to 200 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician or veterinarian.

The following formulations are representative for all of the pharmacologically active compounds of this invention. Example of a suitable capsule formulation:

|  | per capsule, mg |
| --- | --- |
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

|  | per tablet, mg |
| --- | --- |
| Active ingredient, as salt | 10 |
| Avicel | 108 |
| Colloidal silica | 10 |
| Talc | 20 |
| Magnesium stearate | 2 |
| Total | 150 |

Example of a suitable injection formulation:

|  | per 100 ml |
| --- | --- |
| Active ingredient, as salt | 1000 mg |
| Metagin | 0.8 mg |
| Propagin | 0.2 mg |
| HCl 1/10 N to pH 3.5 | 3 ml |
| Aq. sterilisata ad | 100 ml |

The pharmaceutical preparations may also contain therapeutically useful substances other than the pharmacologically active compounds of formula I.

The following examples are intended to illustrate the present invention, without limiting the scope thereof.

EXAMPLE 1

N'-Ethyl-4-benzyl-1-piperazinecarboxamide

To a solution of 13.5 g (0.19 mole) of ethyl isocyanate in 300 ml of ether was added dropwise at 25° C. over a period of 30 minutes 37.0 g (0.21 mole) of 1-benzyl-piperazine. The mixture was refluxed for 2 hours. 250 ml of petroleum ether was added and the mixture was cooled to 5° C. The solid, which precipitated from the solution, was collected by filtration and recrystallised from toluene-petroleum ether 1:1 to give 43 g of N'-ethyl-4-benzyl-1-piperazinecarboxamide. Melting point 100°–102° C.

EXAMPLE 2

N'-Ethyl-N'-methyl-4-bensyl-1-piperazinecarboxamide hydrochloride

To 0.068 mole of lithium diisopropylamide, prepared from n-butyllithium and diisopropylamine in tetrahydrofuran, was added at −40° C. 14.9 g (0.060 mole) of N'-ethyl-4-benzyl-1-piperazinecarboxamide in 100 ml of tetrahydrofuran over a period of 30 minutes. The mixture was warmed to 0° C. during 30 minutes. After cooling to −30° C. 11.6 g (0.082 mole) of methyl iodide was added during 20 minutes. The mixture was allowed to stand at room temperature over night. The mixture was poured onto ice and extracted with ether. The combined extracts were dried over sodium sulphate and the ether removed by distillation. The residual oil was dissolved in ether and the hydrochloride was precipitated with ethanolic HCl. The solid was collected by filtration and recrystallized from isopropanol to give 14.0 g of N'-ethyl-N'-methyl-4-benzyl-1-piperazinecarboxamide hydrochloride.

EXAMPLE 3

N',N'-Diethyl-4-benzyl-1-piperazinecarboxamide

A solution of 26.4 g (0.15 mole) of 1-benzylpiperazine in 70 ml of chloroform was heated until it began refluxing and a solution of 20.4 g (0.15 mole) of diethylcarbamoyl chloride in 80 ml of chloroform was added. The mixture was refluxed for 2 hours. The cooled mixture was made basic with sodium hydroxide (0.25 mole, 10.0 g in 60 ml of water) and extracted with chloroform. The chloroform extracts were dried over sodium sulphate, the solvent removed and the residue distilled to give 25.4 g of N',N'-diethyl-4-benzyl-1-piperazinecarboxamide, b.p. 140°–150° C. at 0.12 mm Hg.

EXAMPLE 4

N'-Ethyl-1-piperazinecarboxamide 22.3 g (0.09 mole) of N'-ethyl-4-benzyl-1-piperazinecarboxamide dissolved in 370 ml of ethanol and acidified with ethanolic HCl was treated with hydrogen over a palladium catalyst in a Parr hydrogenator at 35–40 psi. The catalyst was removed by filtration and the solvent removed under reduced pressure. The residue was dissolved in 25 ml of water and was made basic with 10 g (0.25 mole) of sodium hydroxide in 50 ml of water. The mixture was extracted with chloroform. The combined extracts were dried over sodium sulphate and concentrated. The white product was recrystallised from isobutylacetate to give 10.0 g of N'-ethyl-1-piperazinecarboxamide. Melting point 81°–83° C.

EXAMPLE 5

N'-Ethyl-4-[4,4-(di-p-fluorophenyl)butyl]-1-piperazinecarboxamide hydrochloride

A stirred mixture of 4.7 g (0.03 mole) of N'-ethyl-1-piperazinecarboxamide, 10.1 g (0.036 mole) of 4-chloro-1,1-(di-p-fluorophenyl)butane, 5.0 g of sodium bicarbonate and 10 ml of ethanol was heated at reflux for 60 hours. 50 ml of water was added. The mixture was extracted twice with ether. The combined extracts were dried over sodium sulphate and concentrated. The residue was dissolved in ethanol-ether and the hydrochloride was precipitated with ethanolic HCl. The solid was collected by filtration and recrystallised from 2-butanone-isopropanol 4:1 to give 6.4 g of N'-ethyl-4-[4,4-(di-p-fluorophenyl)butyl]-1-piperazinecarboxamide hydrochloride. Melting point 177°–178° C. Infrared spectrum number 1.

EXAMPLE 6

N'-Methyl-4-[4,4-(di-p-fluorophenyl)butyl]-1-piperazinecarboxamide

To a solution of 20.0 g (0.06 mole) of 1-[4,4-(di-p-fluorophenyl)butyl]-piperazine in 150 ml of ether was added dropwise over a period of 30 minutes 4.5 g (0.079 mole) of methyl isocyanate in 10 ml of ether. The mixture was allowed to stand at room temperature. On short standing a white crystalline precipitate appeared which was collected by filtration and recrystallized from ethanol-ether to give 21.0 g of N'-methyl-4-[4,4-(di-p-fluorophenyl)butyl]-1-piperazinecarboxamide. Melting point 160°–162° C. Infrared spectrum number 2.

EXAMPLE 7

N'-Phenyl-4-[4,4-(di-p-fluorophenyl)butyl]-1-piperazinecarboxamide hydrochloride To a solution of 5.0 g (0.015 mole) of 1-[4,4-(di-p-fluorophenyl)butyl]-piperazine in 30 ml of ether was added dropwise 2.0 g (0.017 mole) of phenyl isocyanate in 2 ml of ether. The mixture was refluxed for 1 hour. After standing over night the mixture was acidified with ethanolic HCl. The solid, which precipitated, was collected by filtration and recrystallised from ethanol to give 5.6 g of N'-phenyl-4-[4,4-(di-p-fluorophenyl)butyl]-1-piperazinecarboxamide hydrochloride. Melting point 202°–204° C.

EXAMPLE 8 trans-2,5-Dimethyl-N'-methyl-4-[4,4-(di-p-fluorophenyl)butyl]-1-piperazinecarboxamide oxalate To a solution of 5.0 g (0.014 mole) of trans-2,5-dimethyl-1-[4,4-(di-p-fluorophenyl)butyl]-piperazine in 25 ml of ether was added dropwise a solution of 0.9 g (0.016 mole) of methyl isocyanate in 5 ml of ether. After stirring for 30 minutes, the mixture was refluxed for 2 hours. The ether was removed under reduced pressure. An analytical sample of the oily residue was isolated by preparative thin layer chromatography (tlc). Preparative tlc was performed on plates covered with a 2.0 mm thick layer of silica gel (Merck $F_{254}$). Eluent, chloroformdiethylamine-methanol (17:2:1). The zone of silica gel containing the product was detected by UV light; scratched of and eluted with ether. $R_f$-value: 0.67. Infrared spectrum number 3.

The oily residue was dissolved in 10 ml of 2-butanone and 2.5 g (0.028 mole) of oxalic acid in 30 ml of 2-butanone was added. The solid which precipitated was collected by filtration and recrystallized from isopropanol to give 4.0 g of a crystalline complex between trans-2,5-dimethyl-N'-methyl-4-[4,4-(di-p-fluorophenyl)butyl]-1-piperazinecarboxamide and oxalic acid containing about 1.5 mole oxalic acid per mole free base and a certain amount of isopropanol which could only be removed by extreme means. Melting point 153°–155° C.

EXAMPLE 9

4-[4,4-(di-p-Fluorophenyl)butyl]-1-piperazinecarboxamide-hydrochloride

To a solution of 5.0 g (0.015 mole) of 1-[4,4-(di-p-fluorophenyl)butyl]-piperazine in 25 ml glacial acetic acid was added dropwise 1.6 g (0.02 mole) of potassium cyanate in 10 ml of water. The mixture was allowed to stand over night at room temperature. The cooled mixture was diluted with 75 ml of water and made basic with 5 N sodium hydroxide. The solid, which precipitated, was collected by filtration, washed with water, and dried. The resulting solid was dissolved in ethanol and the solution was treated with a slight excess of ethanolic HCl. The product, which precipitated, was collected by filtration and recrystallized from ethanol-ether to give 4.7 g of 4-[4,4-(di-p-fluorophenyl)butyl]-1-piperazinecarboxamide hydrochloride. Melting point 195°–197° C.

EXAMPLE 10

N'-Methyl-4-[4,4-(di-p-fluorophenyl)butyl]-1-piperazinecarbothioamide hydrochloride To a solution of 3.3 g (0.01 mole) of 1-[4,4-(di-p-fluorophenyl)butyl]-piperazine in 25 ml of ether was added dropwise a solution of 0.75 g (0.01 mole) methyl isothiocyanate in 5 ml of ether. The mixture was allowed to stand with stirring over night. The ether was removed under reduced pressure. The oily residue was dissolved in ethanol, and converted to the salt by addition of ethanolic HCl. Ether was added, and the solid, which precipitated, collected by filtration. The salt was recrystallized from methanol to give 3.5 g of N'-methyl-4-[4,4-(di-p-fluorophenyl)butyl]-1-piperazinecarbothioamide hydrochloride. Melting point 214°–216° C. Infrared spectrum number 4.

FIGS. 1 to 4 correspond to infrared spectrums 1 to 4 of Examples 5, 6, 8, and 10.

TABLE II

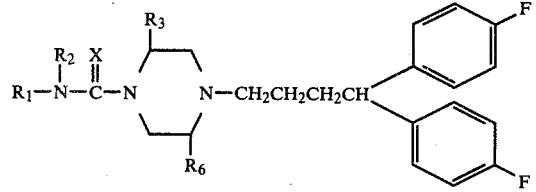

| Example | Method in accordance with example | $R_1$ | $R_2$ | $R_3$ | $R_6$ | X | M.p.[a] °C. | Salt |
|---|---|---|---|---|---|---|---|---|
| 11 | 6 + 2 | $CH_3$ | $CH_3$ | H | H | O | 129–31 | HCl |
| 12 | 1 + 2 + 4 + 5 | $CH_3$ | $C_2H_5$ | H | H | O | 152–53 | HCl |
| 13 | 3 + 4 + 5 | $C_2H_5$ | $C_2H_5$ | H | H | O | 203–05 | oxalate |
| 14 | 7 | $C_2H_5$ | H | $CH_3$[b] | $CH_3$[b] | O | 184–86 | HCl |
| 15 | 10 | $C_2H_5$ | H | H | H | S | 197–99 | HCl |

TABLE II-continued

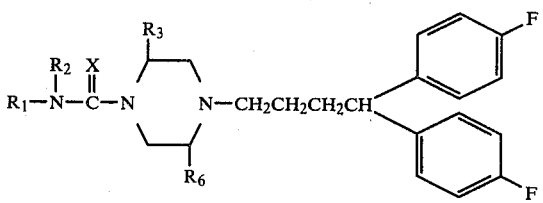

| Example | Method in accordance with example | $R_1$ | $R_2$ | $R_3$ | $R_6$ | X | M.p.[a] °C. | Salt |
|---|---|---|---|---|---|---|---|---|
| 16 | 7 | n-$C_3H_7$ | H | H | H | O | 190-92 | HCl |
| 17 | 10 | n-$C_3H_7$ | H | H | H | S | 185-87 | HCl |
| 18 | 1 + 4 + 5 | iso-$C_3H_7$ | H | H | H | O | 206-08 | HCl |
| 19 | 7 | iso-$C_3H_7$ | H | $CH_3$[b] | $CH_3$[b] | O | 184-86 | HCl |
| 20 | 10 | iso-$C_3H_7$ | H | H | H | S | 202-04 | HCl |
| 21 | 7 | cyclo-$C_3H_5$ | H | H | H | O | 192-94 | HCl |
| 22 | 7 | cyclo-$C_3H_5$ | H | $CH_3$[b] | $CH_3$[b] | O | 172-75 | HCl |
| 23 | 10 | cyclo-$C_3H_5$ | H | H | H | S | 187-89 | HCl |
| 24 | 7 | n-$C_4H_9$ | H | H | H | O | 185-87 | HCl |
| 25 | 10 | n-$C_4H_9$ | H | H | H | S | 156-58 | HCl |
| 26 | 7 | tert-$C_4H_9$ | H | H | H | O | 191-93 | HCl |
| 27 | 7 | $CH_2$—cyclo-$C_3H_5$ | H | H | H | O | 196-98 | HCl |
| 28 | 7 | n-$C_5H_{11}$ | H | H | H | O | 172-74 | HCl |
| 29 | 7 | cyclo-$C_6H_{11}$ | H | H | H | O | 172-73 | HCl[c] |
| 30 | 7 | n-$C_8H_{17}$ | H | H | H | O | 187-89 | HCl |
| 31 | 7 | $CH_2$=$CHCH_2$ | H | H | H | O | 187-89 | HCl |
| 32 | 10 | $C_6H_5$ | H | H | H | S | 206-08 | HCl |
| 33 | 7 | p-Cl—$C_6H_4$ | H | H | H | O | 116-18 | HCl |
| 34 | 7 | $CH_2$—$C_6H_5$ | H | H | H | O | 185-87 | HCl |
| 35 | 7 | $CH_2CH_2$—$C_6H_5$ | H | H | H | O | 139-41 | HCl |

[a]Melting points are uncorrected
[b]trans-2,5-dimethyl
[c]Hydrate (about one $H_2O$)

EXAMPLE 36

N'-ethyl-4-[4,4-(di-p-fluorophenyl)butyl]-1-piperazinecarboxamide hydrochloride

A stirred mixture of 9,9 g (0,03 mole) of 1-[4,4-(di-p-fluorophenyl)butyl]piperazine, 5,0 g (0,03 mole) of phenyl N-ethylcarbamate, 6,6 g of potassium carbonate and 100 ml of toluene was heated at reflux for 45 minutes. The mixture was filtered and the solvent was removed. The residual oil was dissolved in ethanol-ether and the hydrochloride was precipitated with ethanolic HCl. The solid was collected by filtration and recrystallized from 2-butanone-isopropanol 4:1 to give 6,8 g of N'-ethyl-4-[4,4-(di-p-fluorophenyl)butyl]-1-piperazinecarboxamide hydrochloride. Melting point 177°-178° C.

What we claim is:

1. A compound, characterized in that it has the general formula

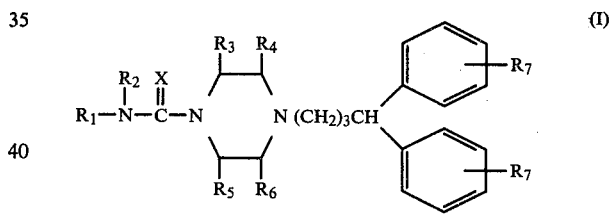

wherein $R_1$ and $R_2$ are groups independently selected from the group of hydrogen, alkyl straight or branched chains having from 1 to 10 carbon atoms, cycloalkyl having from 3 to 8 carbon atoms, aralkyl having from 7 to 9 carbon atoms, alkenyl having from 2 to 10 carbon atoms, phenyl unsubstituted or substituted by one to three substituents selected from halogen, including F, Cl and Br, lower alkyl having from 1 to 5 carbon atoms, lower alkoxy having from 1 to 5 carbon atoms, amine unsubstituted or substituted by one or two lower alkyl groups having from 1 to 5 carbon atoms, —$CF_3$ and —CN groups, $R_3$, $R_4$, $R_5$ and $R_6$ are groups independently selected from hydrogen, lower alkyl having from 1 to 3 carbon atoms and phenyl, $R_7$ is a group selected from hydrogen, halogen including F, Cl and Br, lower alkoxy having from 1 to 3 carbon atoms and —$CF_3$ groups, and X is O or S, and pharmaceutically acceptable acid addition salts thereof.

2. A compound of claim 1 wherein $R_1$ and $R_2$ independently are selected from the group consisting of hydrogen and alkyl containing from 1 to 10 carbon atoms.

3. A compound of claim 1 wherein $R_1$ and $R_2$ independently are hydrogen or cycloalkyl containing from 3 to 8 carbon atoms.

* * * * *